(12) United States Patent
Wei et al.

(10) Patent No.: US 9,564,536 B2
(45) Date of Patent: Feb. 7, 2017

(54) SELF-ALIGNED METAL OXIDE THIN-FILM TRANSISTOR COMPONENT AND MANUFACTURING METHOD THEREOF

(71) Applicant: SHENZHEN ROYOLE TECHNOLOGIES CO., LTD., Shenzhen (CN)

(72) Inventors: Peng Wei, Shenzhen (CN); Xiaojun Yu, Shenzhen (CN); Zihong Liu, Shenzhen (CN)

(73) Assignee: SHENZHEN ROYOLE TECHNOLOGIES CO., LTD., Shenzhen (CN)

( * ) Notice: Subject to any disclaimer, the term of this patent is extended or adjusted under 35 U.S.C. 154(b) by 0 days.

(21) Appl. No.: 14/648,628

(22) PCT Filed: Nov. 30, 2012

(86) PCT No.: PCT/CN2012/085643
§ 371 (c)(1),
(2) Date: May 29, 2015

(87) PCT Pub. No.: WO2014/082292
PCT Pub. Date: Jun. 5, 2014

(65) Prior Publication Data
US 2015/0303308 A1    Oct. 22, 2015

(51) Int. Cl.
*H01L 29/10* (2006.01)
*H01L 29/786* (2006.01)
(Continued)

(52) U.S. Cl.
CPC ....... *H01L 29/7869* (2013.01); *H01L 27/1225* (2013.01); *H01L 29/66969* (2013.01)

(58) Field of Classification Search
CPC ........... H01L 29/7869; H01L 29/66969; H01L 27/1225; H01L 27/1288; H01L 29/41733; H01L 29/66742; H01L 21/308; H01L 21/47573; H01L 27/3262
(Continued)

(56) References Cited

U.S. PATENT DOCUMENTS

| | | | | | |
|---|---|---|---|---|---|
| 4,700,458 | A | * | 10/1987 | Suzuki | H01L 29/66765 148/DIG. 106 |
| 2005/0219434 | A1 | * | 10/2005 | Sakurai | H01L 27/1288 349/42 |

(Continued)

FOREIGN PATENT DOCUMENTS

| | | |
|---|---|---|
| CN | 101465355 | 6/2009 |
| CN | 101867017 | 10/2010 |
| CN | 102405517 | 4/2012 |
| CN | 102655095 | 9/2012 |

OTHER PUBLICATIONS

International Search Report of PCT/CN2012/085643, dated Sep. 12, 2013 and English language translation (6 pages total).

*Primary Examiner* — Benjamin Sandvik
*Assistant Examiner* — Herve Assouman
(74) *Attorney, Agent, or Firm* — Hamre, Schumann, Mueller & Larson, P.C.

(57) ABSTRACT

The present invention is applicable to the field of electronic component technologies and provides a manufacturing method of a self-aligned metal oxide TFT component, including: selecting a substrate and preparing a gate on the substrate; successively disposing an insulation layer, a transparent electrode layer, and a photoresist on the gate; using the gate as a mask to perform exposure from a back side of the substrate, so as to form a source and a drain that are aligned with the gate; depositing a metal oxide semiconductor layer on the transparent electrode layer; performing etching on the semiconductor layer, the source, and the drain, so that outer ends of the source and the drain are exposed out of the metal oxide semiconductor layer; and
(Continued)

depositing a passivation layer and leading out the source and the drain. In the present invention, a transparent conductor is used as the electrode layer, and a bottom gate is used as a mask to perform back exposure, so as to perform etching on the source and the drain, thereby implementing a self-alignment between the source or the drain and the gate, effectively reducing parasitic capacitance, and improving component performance. The component is of a bottom-gate bottom-contact structure, and there is no need to manufacture an etch-stop layer, thereby simplifying a process, reducing use of a photolithographic mask, improving production efficiency, and improving an electrical property of the component.

8 Claims, 8 Drawing Sheets

(51) Int. Cl.
    *H01L 29/66*     (2006.01)
    *H01L 27/12*     (2006.01)

(58) Field of Classification Search
    USPC .......................................................... 257/43
    See application file for complete search history.

(56) References Cited

U.S. PATENT DOCUMENTS

2011/0263091 A1* 10/2011 Yamazaki ........... H01L 27/1225
    438/287
2011/0297930 A1* 12/2011 Choi ................. G02F 1/133345
    257/43

* cited by examiner

SELF-ALIGNED METAL OXIDE THIN-FILM TRANSISTOR COMPONENT AND MANUFACTURING METHOD THEREOF

TECHNICAL FIELD

The present invention pertains to the field of electronic component technologies, and in particular, to a self-aligned metal oxide thin-film transistor component and a manufacturing method thereof.

BACKGROUND

Figure 1:
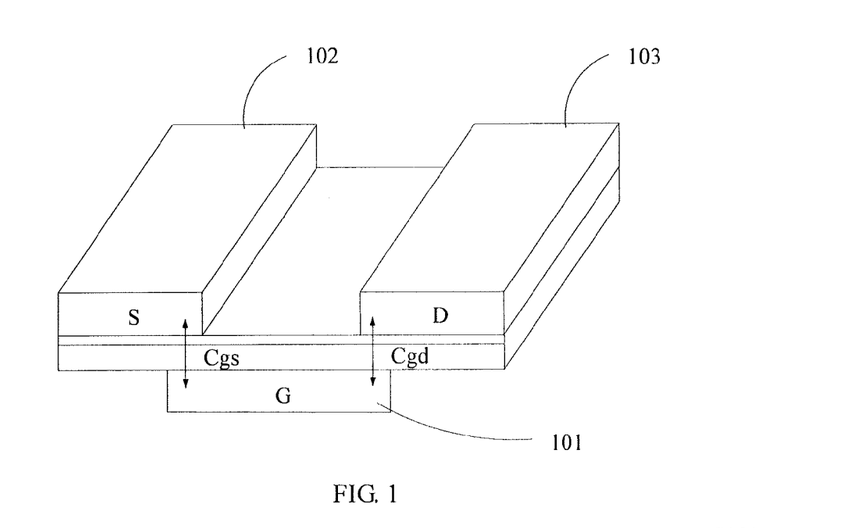
FIG. 1 is a schematic structural diagram of an existing metal oxide thin-film transistor component.

A metal oxide thin-film transistor (TFT) is a basic circuit component that may be widely used in various electronic systems, and it has many advantages, such as high electron mobility, a low-temperature manufacturing process, relatively high stability, and high transparency. As shown in FIG. 1, in a conventional TFT manufacturing process, an alignment between a gate (Gate) 101 and a source (Source) 102 or a drain (Drain) 103 that are of the TFT component is implemented by using two layers of different mask plates and in a manual or mechanical optical alignment manner. Restricted by factors such as precision of an alignment device, this manner results in that the source 102 and the drain 103 overlap the gate 101, thereby causing relatively large gate-source parasitic capacitance (Cgs) and gate-drain parasitic capacitance (Cgd). The relatively large parasitic capacitance generally reduces a cut-off frequency of the component (a cut-off frequency is in an inverse proportion to parasitic capacitance), thereby reducing a running speed of a circuit; in addition, the relatively large parasitic capacitance also causes that voltage of a display electrode departs from a design requirement, so that a complicated gate drive circuit is required to compensate a deviation, which increases complexity of a circuit design; in addition, parasitic capacitance that cannot be precisely controlled also increase complexity and uncertainty of the circuit design, and a minimum size of a channel (Channel) cannot be precisely controlled, thereby limiting size minimization of the channel, and making it difficult to improve performance of the component. In addition, use of a multilayer mask plate in a conventional component also increases process complexity and costs, which is unfavorable to improvement of production efficiency.

To resolve the foregoing problems, the prior art proposes a self-aligned component that is designed by using a specified process and may automatically align the source and the drain with the gate in a manufacturing process, and there is no need to align two layers of different mask plates in a manual manner or through mechanical optics, an alignment between the source or the drain and the gate may be implemented. This type of self-aligned component is widely applied to a conventional monocrystalline silicon chip (MOSFET) manufacturing process; however, a self-aligned process of the transistor in the conventional silicon chip cannot be directly applied to the metal oxide TFT.

To resolve this problem, a self-aligned process is proposed in the prior art, in which a top gate is used as a mask, an automatic alignment is performed to form the source and the drain, Ar plasma, or NH3 plasma that has more hydrogen is used to process a surface of the metal oxide of indium gallium zinc oxide (IGZO), so as to reduce contact resistance of the source and the drain region. However, the Ar plasma only partially improves surface resistance of a source area, a drain area and a metal contact, but resistance of the source area and the drain area is still large, and the plasma needs additional technological processing, which increases costs; the hydrogen can spread to the channel, which degrades the device reliability and causes that the source area and the drain area are extended to the channel, an overlapped area of the gate and the source and an overlapped area of the gate and the drain increase, and parasitic capacitance increases, thereby reducing performance of the metal oxide TFT component.

In another existing self-aligned process, for example, the Chinese Patent Application No. CN201080017247, an etch-stop layer needs to be formed on a semiconductor layer; the etch-stop layer, a source and a drain are separately formed through two times of exposure, so that two times of back exposure and self-alignment increase use of a photolithographic mask and greatly increase difficulty in implementing the process. In addition, the etch-stop layer also produces an adverse effect on a semiconductor channel, thereby affecting an electrical property of a TFT.

For another example, the Chinese Patent Application No. CN201110147134 discloses a TFT manufacturing process, in which a grey-tone mask is used. By changing exposure, one set of mask plate is used to separately implement preparation of a source, a drain, and a semiconductor channel. However, a size of the channel is strictly restricted by specifications of the mask aligner, and the exposure needs to be relatively precisely controlled to distinguish the source and the drain from the semiconductor channel, so that the TFT manufacturing process is subject to a relatively large restriction and is relatively difficult to be applied, and in addition, which is unfavorable to reduction of preparation costs.

SUMMARY

An objective of the present invention is to provide a manufacturing method of a self-aligned metal oxide thin-film transistor component, so as to resolve a problem that parasitic capacitance is easily generated and a process is complicated in a conventional method.

The present invention is implemented as follows: a manufacturing method of a self-aligned metal oxide thin-film transistor component includes the following steps:

selecting a substrate and preparing a gate on the substrate;

successively disposing an insulation layer, a transparent electrode layer, and a photoresist on the gate;

using the gate as a mask to perform exposure from a back side of the substrate, and removing a part that is of the transparent electrode layer and is aligned with the gate, so as to form a source and a drain that are aligned with the gate;

depositing a metal oxide semiconductor layer on the source and the drain;

performing etching on the metal oxide semiconductor layer, the source, and the drain, so that outer ends of the source and the drain are exposed out of an etched metal oxide semiconductor layer, and isolating a drain from a source of a different thin-film transistor component; and depositing a passivation layer on the substrate, and leading the source and the drain out of the passivation layer.

Another objective of the present invention is to provide a self-aligned metal oxide thin-film transistor component, including:

a substrate;

a gate and an insulation layer, which are successively disposed on the substrate in a stack manner;

a source and a drain, which are disposed on the insulation layer side by side and are transparent electrodes;

a metal oxide semiconductor layer, which is disposed on the source and the drain and forms a channel between the source and the drain, where two sides of the channel are aligned with inner sides of the source and the drain; and a passivation layer, which is packaged at a side of the substrate on which the gate is disposed, where:

the source and the drain are led out of the passivation layer by using a conducting material.

Still another objective of the present invention is to provide a manufacturing method of a self-aligned metal oxide thin-film transistor pixel circuit, including the following steps:

selecting a substrate and preparing a gate, a gate lead, and a storage capacitor electrode on the substrate;

successively disposing an insulation layer, a transparent electrode layer, and a photoresist on the gate, the gate lead, and the storage capacitor electrode;

using the gate, the gate lead, and the storage capacitor electrode as a mask to perform exposure from a back side of the substrate, and removing parts that are of the transparent electrode layer and are aligned with the gate, the gate lead, and the storage capacitor electrode, so as to form a source and a drain that are aligned with the gate;

depositing a metal oxide semiconductor layer on the source, the drain, and the other reserved part of the transparent electrode layer;

performing etching on the metal oxide semiconductor layer, the source, and the drain, so that outer ends of the source and the drain are exposed out of an etched metal oxide semiconductor layer, and isolating a drain from a source of a different thin-film transistor component; and depositing a passivation layer on the substrate, and leading the source, the drain, and the gate lead out of the passivation layer.

Yet another objective of the present invention is to provide a self-aligned metal oxide thin-film transistor pixel circuit, including:

a substrate;

a gate, a gate lead, and a storage capacitor electrode, which are disposed on the substrate side by side;

an insulation layer, which is disposed on the gate and the storage capacitor electrode;

a source and a drain, which are transparent electrodes and are disposed side by side on an area that is on the insulation layer and corresponding to the gate;

a metal oxide semiconductor layer, which is disposed on the source and the drain and forms a channel between the source and the drain, where two sides of the channel are aligned with inner sides of the source and the drain; and a passivation layer, which is packaged at a side of the substrate on which the gate is disposed, where:

the source, the drain, and the gate lead are led out of the passivation layer by using a conducting material. The present invention has the following beneficial effects:

In one aspect, in this method, a bottom gate is used as a mask to perform back exposure, so that a high-precision self-alignment between a source or a drain and a channel and a high-precision self-alignment between a source or a drain and a gate are implemented, a width of an overlapped area of the source and the gate and a width of an overlapped area of the drain and the gate can be precisely controlled to be less than 2 μm, which is far higher than alignment precision of a conventional mask, thereby effectively reducing parasitic capacitance, improving a circuit speed of the component, controlling a channel in a more precise size, helping implement a minimum size of the channel, and improving component performance; in addition, an alignment of a mask plate in a manufacturing procedure is no longer a crucial alignment requirement, thereby reducing manufacturing difficulty.

In another aspect, the component is of a bottom-gate bottom-contact structure, and an etching process is no longer performed on a semiconductor layer, so that an etch-stop layer does not need to be manufactured, and only one step of the back exposure is required, thereby simplifying a process, reducing use of a photolithographic mask, improving production efficiency, and avoiding an adverse effect of the etch-stop layer to the semiconductor channel; in addition, use of the bottom-contact structure makes it easy to transmit a carrier, thereby improving an electrical property of the component.

In addition, compared with an etching method performed by using a mask plate whose width is less than a resolution gap of a mask aligner, in the present invention, use of a high-precision and expensive mask plate is not required, a size of the channel is not strictly limited to a photolithography device, the manufacturing process is easy to implement, and in addition, another process problem of an alignment by using a conventional mask plate is resolved, and the manufacturing process is suitable for a wide range of applications.

BRIEF DESCRIPTION OF DRAWINGS

FIG. 3-1 to FIG. 3-10 are schematic structural diagrams of all steps in the manufacturing method of the self-aligned metal oxide thin-film transistor component according to the first embodiment of the present invention;

FIG. 4 is a schematic structural diagram of the self-aligned metal oxide thin-film transistor component according to the first embodiment of the present invention;

FIG. 6-1 to FIG. 6-10 are schematic structural diagrams of all steps in the manufacturing method of the self-aligned metal oxide thin-film transistor pixel circuit according to the second embodiment of the present invention.

DESCRIPTION OF EMBODIMENTS

To make the objectives, technical solutions, and advantages of the present invention clearer and more comprehensible, the following further describes the present invention in detail with reference to the accompanying drawings and embodiments. It should be understood that the specific embodiments described herein are merely used to explain the present invention but are not intended to limit the present invention.

The following describes specific implementation of the present invention in detail with reference to specific embodiments.

Figure 2:
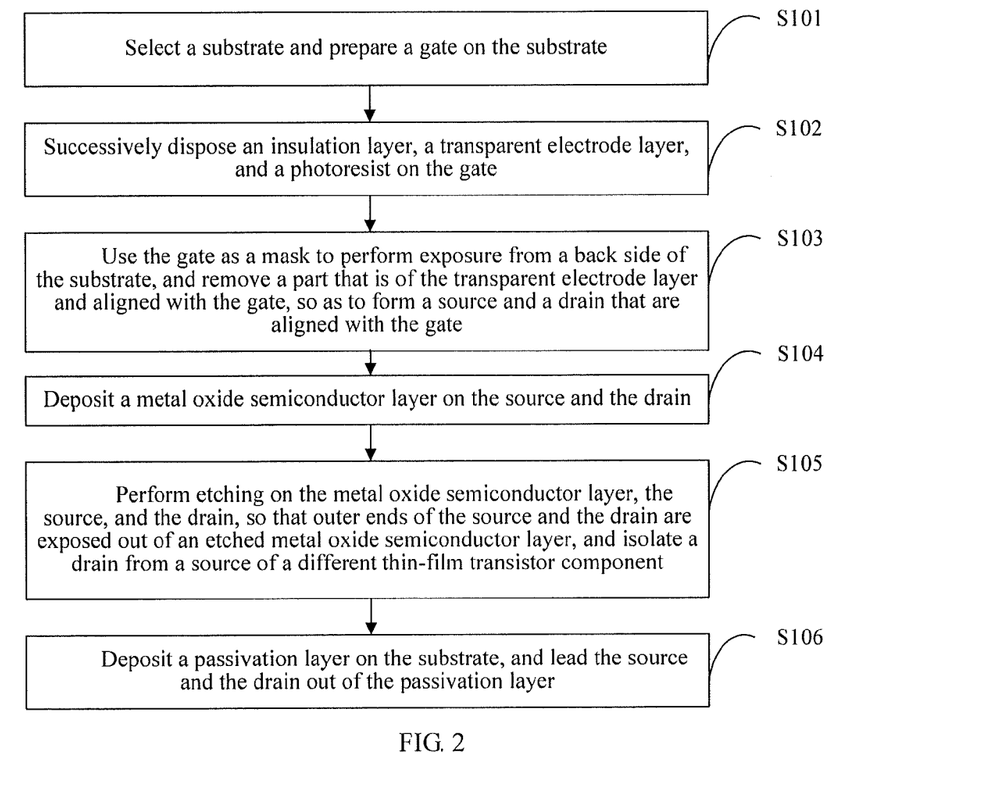
FIG. 2 is a flowchart of a manufacturing method of a self-aligned metal oxide thin-film transistor component according to a first embodiment of the present invention.

FIG. 2 shows a flowchart of a manufacturing method of a self-aligned metal oxide thin-film transistor component according to a first embodiment of the present invention, and FIGS. 3-1 to 3-10 show schematic structural diagrams corresponding to the manufacturing method. For ease of description, only a part relevant to this embodiment is shown.

Figure 31:
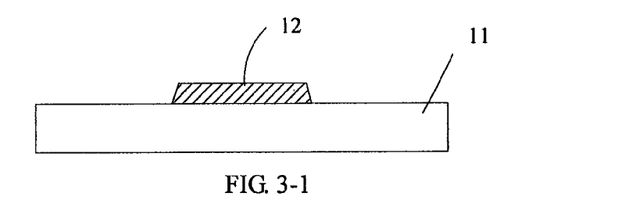

As shown in FIG. 2, the method includes the following steps:

In step S101, a substrate 11 is selected and a gate 12 is prepared on the substrate 11, as shown in FIG. 3-1.

In this step, a transparent material is selected to manufacture the substrate 11, and "transparent" in this embodiment refers to a material, used in a photolithographic process, whose optical wave is transparent, and then a first photolithographic mask is used to manufacture the gate 12. Optionally, a buffer layer may further be disposed on the substrate 11.

Figure 32:
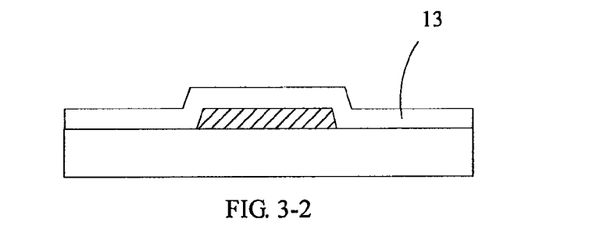
Figure 33:
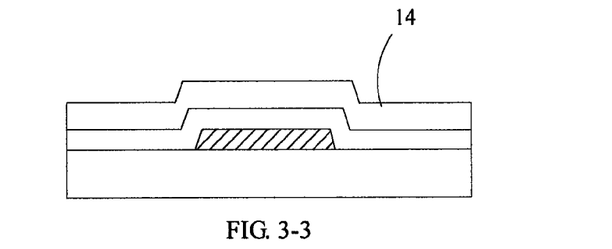
Figure 34:
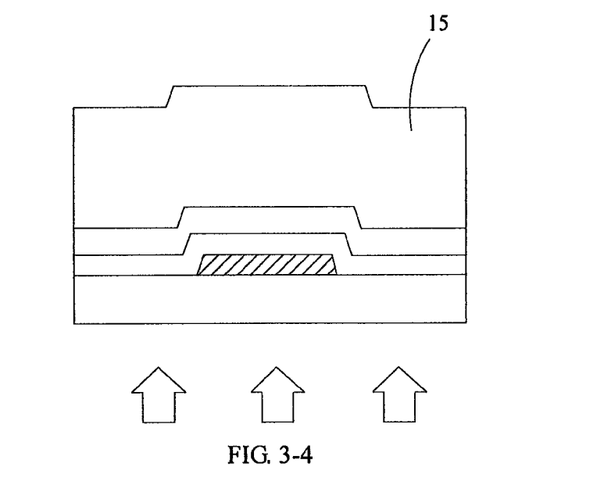

In step S102, an insulation layer 13, a transparent electrode layer 14, and a photoresist 15 are successively disposed on the gate 12, as shown in FIGS. 3-2, 3-3, and 3-4.

In this step, the insulation layer 13 is first deposited on the substrate 11 and the gate 12, as shown in FIG. 3-2. The insulation layer 13 may be a transparent film structure of a SiO2 film, a SiNX film, a multilayer film distributed by SiO2 and SiNX, in a stack manner, or the like. After the insulation layer 13 is deposited, the transparent electrode layer 14 is deposited on the insulation layer 13, as shown in FIG. 3-3. Specifically, a transparent conducting material such as ITO, IZO, or GZO may be selected. Then, the photoresist 15 is coated on the transparent electrode layer 14 for subsequent photolithography use, as shown in FIG. 3-4.

Figure 35:
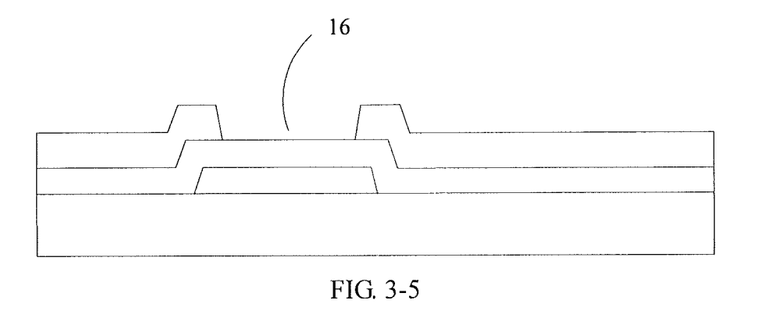

In step S103, the gate 12 is used as a mask to perform exposure from a back side of the substrate 11, and a part that is of transparent electrode layer 14 and is aligned with the gate 12 is removed, so as to form a source 141 and a drain 142 that are aligned with the gate 12, as shown in FIGS. 3-4 and 3-5.

In this embodiment, because a metal material used in the gate 12 is non-transparent, and all other structures are made of transparent materials, the gate 12 may be used as a mask to perform photolithography on the transparent electrode layer 14, so as to prepare the source 141 and the drain 142. Specifically, in this step, the gate 12 is used as a mask to perform exposure and development from the back side of substrate 11, an exposed transparent electrode layer 14 is cured and kept, and a non-exposed part aligned with the gate 12 is peeled off together with the photoresist 15, where an area above the gate 12 is a reserved channel 16, and the source 141 and the drain 142 implement a good self-alignment with the gate 12.

Figure 36:
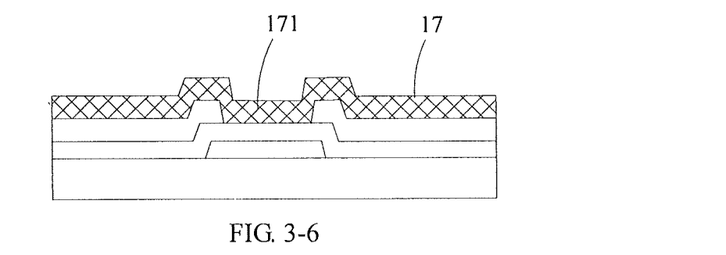

In step S104, a metal oxide semiconductor layer 17 is deposited on the source 141 and the drain 142, as shown in FIG. 3-6.

In this step, the deposited metal oxide semiconductor layer 17 covers the source 141, the drain 142, and the reserved channel in the foregoing step, so as to form a semiconductor channel 171, which is mainly used as a carrier transmission path between the source and the drain, and IGZO, or the like may be selected as a specific material of the semiconductor channel.

Figure 37:
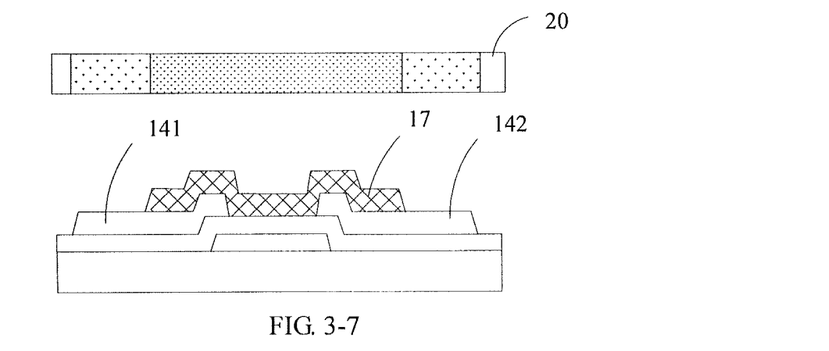

In step S105, the metal oxide semiconductor layer 17, the source 141, and the drain 142 are etched, so that outer ends of the source 141 and the drain 142 are exposed out of an etched metal oxide semiconductor layer 17, and in addition, a drain is isolated from a source of a different thin-film transistor component, as shown in FIG. 3-7.

As a preferred implementation manner of this embodiment, a second photolithographic mask, that is, a gray-tone mask 20 may be used to perform etching on the source 141, the drain 142, and the metal oxide semiconductor layer 17. The gray-tone mask 20 provides a variable transmittance at a different position of a plane of the mask plate. In this embodiment, a suitable gray-tone mask is selected to enable an area of a corresponding transmittance to perform a proper alignment with the to-be-etched source 141, drain 142, and metal oxide semiconductor layer 17, and exposure is performed from a front side of the substrate 11 to perform etching on a large part of the metal oxide semiconductor layer 17, a smaller part of the source 141, and a smaller part of the drain 142, where a reserved metal oxide semiconductor layer 17, source, and drain are in a ladder structure, and the outer ends of the source 141 and the drain 142 are exposed out of the reserved metal oxide semiconductor layer 17. In addition, manufacturing of the component is that multiple TFT components are manufactured in one manufacturing process, and after the foregoing etching is performed, the drain is isolated from the source of the different thin-film transistor component.

In this step, a gray-tone mask is used to implement etching on the metal oxide semiconductor layer 17, the source 141, and the drain 142 at the same time, and compared with a method for separately performing etching on a metal oxide semiconductor layer, a source, and a drain, a photolithography step is reduced and use of one photolithographic mask is reduced, which saves materials, simplifies a process, and also helps improve production efficiency.

Figure 38:
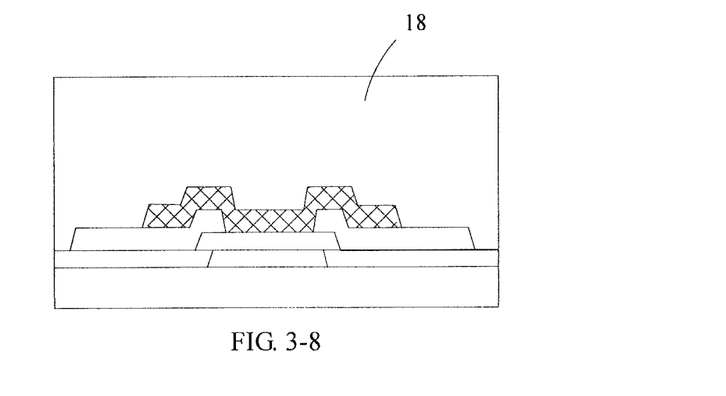
Figure 39:
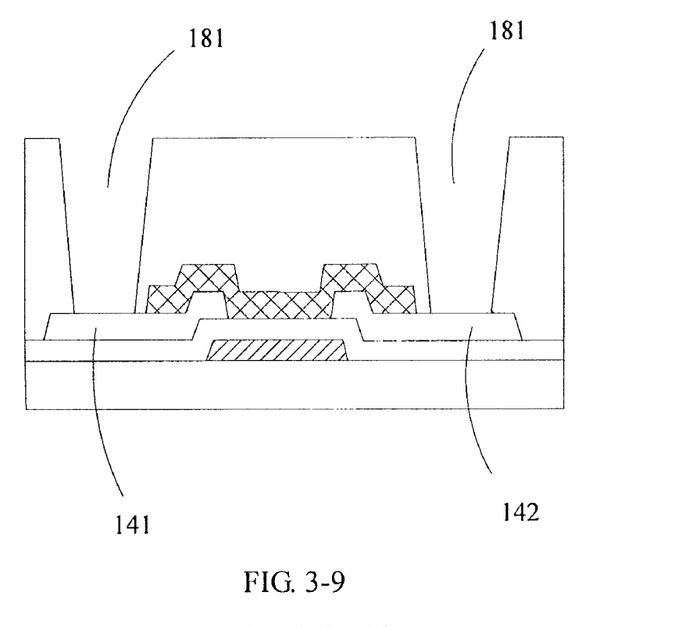
Figure 310:
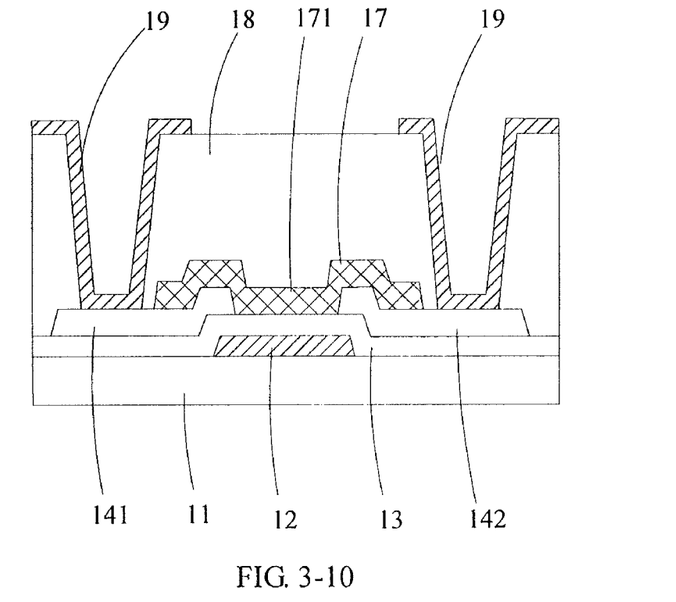

In step S106, a passivation layer 18 is deposited on the substrate 11, and the source 141 and the drain 142 are led out of the passivation layer 18, as shown in FIGS. 3-8, 3-9, and 3-10.

As one implementation manner of this embodiment, a third photolithographic mask may be used to perform etching on the passivation layer 18, so as to form a via 181 to a part of the source 141 that is exposed out of the metal oxide semiconductor layer 17 and a via 181 to a part of the drain 142 that is exposed out of the metal oxide semiconductor layer 17, and then a conducting material 19 is deposited to the passivation layer 18, where the conducting material is preferably a transparent conducting material, such as a transparent metal oxide, and the conducting material 19 covers the passivation layer 18 and is injected into the vias 181 to be in contact with the source 141 and the drain 142. Then, a fourth photolithographic mask is used to perform etching on the conducting material 19, so as to form a conducting lead to lead out the source 141 and the drain 142.

After the foregoing step is performed, the self-aligned metal oxide TFT component is manufactured. It may be understood that the foregoing describes only a manufacturing process of a main structure of the metal oxide thin-film transistor component, and certainly, the component further includes another regular function structure, and the component may be manufactured by using a regular method, which is not described again in the present invention.

In this embodiment of the present invention, a non-transparent bottom gate is used as a mask, and a source and a drain are automatically aligned with a semiconductor channel through back exposure, so that a self-aligned metal oxide TFT component with a bottom-gate bottom-contact structure is manufactured. This method has the following effects:

In one aspect, the bottom gate is used as a mask to perform the back exposure, so that a high-precision self-alignment can be implemented between the source or the drain, and the gate, a width of an overlapped area of the source and the gate and a width of an overlapped area of the drain and the gate can be precisely controlled to be less than 2 μm, which is far higher than alignment precision of a conventional mask, thereby effectively reducing parasitic capacitance, improving a circuit speed of the component, controlling a channel in a more precise size, helping implement a minimum size of the channel, and improving component performance; in addition, an alignment of a mask plate in a manufacturing procedure is no longer a crucial alignment requirement, thereby reducing manufacturing difficulty.

In another aspect, the component is the bottom-gate bottom-contact structure, and an etching process is not further required to be performed on a semiconductor layer, so that an etch-stop layer does not need to be manufactured, and only one step of the back exposure is required, thereby simplifying a process, reducing use of a photolithographic mask, improving production efficiency, and avoiding an adverse effect of the etch-stop layer on the semiconductor channel; in addition, use of the bottom-contact structure makes it easy to transmit a carrier among the source, the semiconductor channel, and the drain, thereby improving an electrical property of the component.

In still another aspect, when a gray-tone mask is used to perform etching on the source, the drain, and the semiconductor channel, one step of the photolithographic process may be reduced and the use of the photolithographic mask may be reduced, thereby reducing costs and improving the production efficiency.

In addition, compared with an etching method performed by using a mask plate whose width is less than a resolution gap of a mask aligner, in the present invention, use of a high-precision and expensive mask plate is not required, a size of the channel is not strictly limited to a photolithography device, the manufacturing process is easy to implement, and in addition, another process problem of an alignment by using a conventional mask plate is resolved.

Based on the foregoing manufacturing method, an embodiment of the present invention further provides a self-aligned metal oxide thin-film transistor component, which may be manufactured by using the foregoing manufacturing process.

Figure 4:
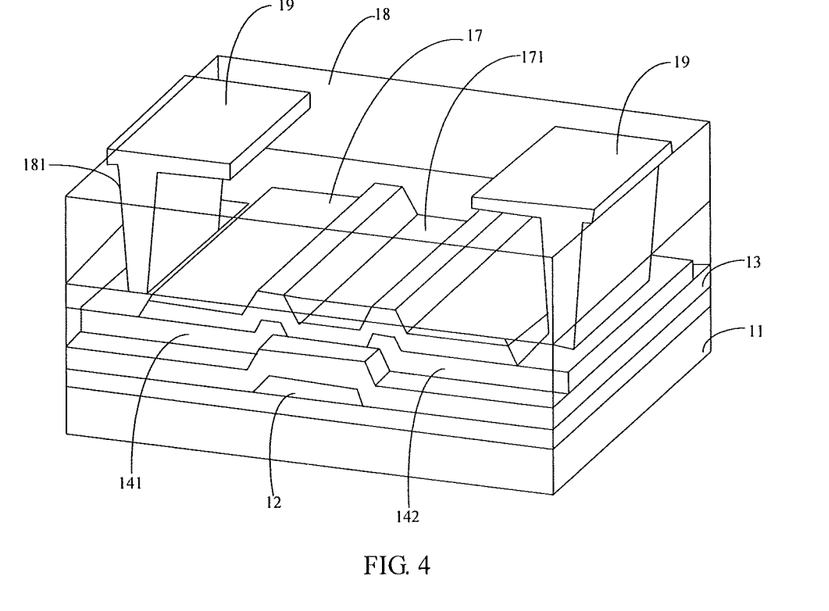

Referring to FIG. 4, the component is a TFT component with a bottom-gate bottom-contact structure, and mainly includes a substrate 11. A gate 12 and an insulation layer 13 are successively disposed on the substrate 11 in a stack manner, a transparent source 141 and a transparent drain 142 are disposed on a surface of the insulation layer 13 side by side, in this case, a metal oxide semiconductor layer 17 is on the source 141 and the drain 142, the metal oxide semiconductor layer 17 forms a semiconductor channel 171 that is between the source 141 and the drain 142 and may be used to transmit a carrier, and two sides of the semiconductor channel 171 are aligned with inner sides of the source 141 and the drain 142. In addition, a passivation layer 18 is disposed on the substrate 11, and all structures on the substrate 11 are sealed within the passivation layer. The source 141 and the drain 142 are led out of the passivation layer 18 by using a conducting material 19, so as to implement an electrical connection to an external circuit.

Further, the metal oxide semiconductor layer 17 may cover a part of the source 141 and a part of the drain 142, so that outer ends of the source 141 and the drain 142 are exposed out of the metal oxide semiconductor layer 17, and further preferably, the outer ends are exposed out of the metal oxide semiconductor layer 17 in a mutual symmetry manner. In addition, a via 181 to an exposed part of the source 141 and a via to an exposed part of the drain 142 may be disposed on the passivation layer 18, where the vias 181 are filled with transparent conducting materials 19, and the source 141 and the drain 142 are led out of the passivation layer 18.

Further, the foregoing back exposure process is used, so that a width of an overlapped area of the source 141 and the semiconductor channel 171 that are of the component and a width of an overlapped area of the drain 142 and the semiconductor channel 171 that are of the component may be reduced to be less than 2 μm, which is far less than that of an overlapped area of a conventional component, thereby effectively reducing parasitic capacitance and improving component performance.

It may be understood that the self-aligned metal oxide thin-film transistor component may further include another function structure, and details are not described again in this embodiment. In addition, any metal oxide thin-film transistor component manufactured by using the foregoing method shall fall within the protection scope of the present invention.

Embodiment 2

Figure 5:
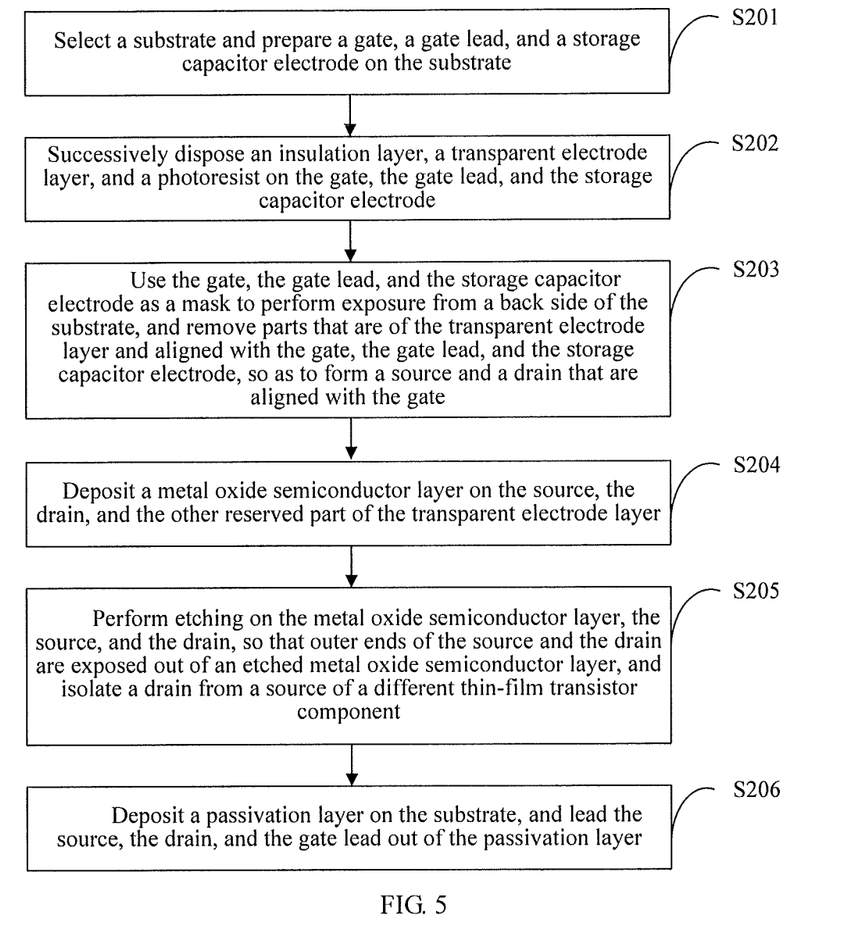
FIG. 5 is a flowchart of a manufacturing method of a self-aligned metal oxide thin-film transistor pixel circuit according to a second embodiment of the present invention.

FIG. 5 shows a flowchart of a manufacturing method of a self-aligned metal oxide thin-film transistor pixel circuit according to a second embodiment of the present invention. FIGS. 6-1 to 6-10 show schematic structural diagrams corresponding to the manufacturing method. For ease of description, only a part relevant to this embodiment is shown.

Figure 61:
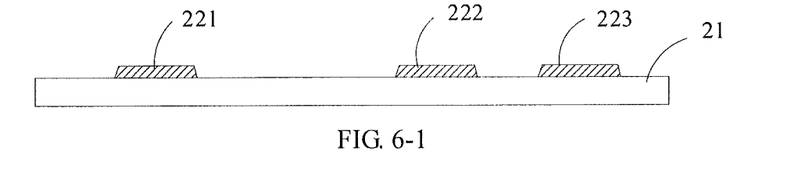

As shown in FIG. 5, the method includes the following steps:

In step S201, a substrate 21 is selected, and a gate 221, a gate lead 222, and a storage capacitor electrode 223 are prepared on the substrate 21, as shown in FIG. 6-1.

In this step, a transparent material is selected to manufacture the substrate 21, and "transparent" in this embodiment refers to a material, used in a photolithographic process, whose optical wave is transparent, and then a first photolithographic mask is used to manufacture the gate 221, the gate lead 222, and the storage capacitor electrode 223. Optionally, a buffer layer may further be disposed on the substrate 21 first.

Figure 62:
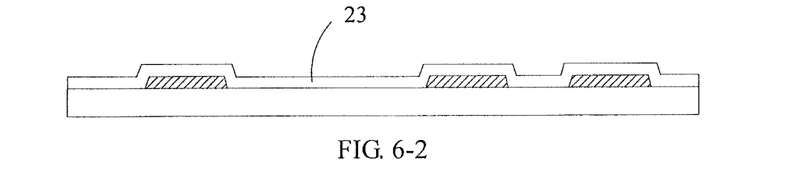
Figure 63:
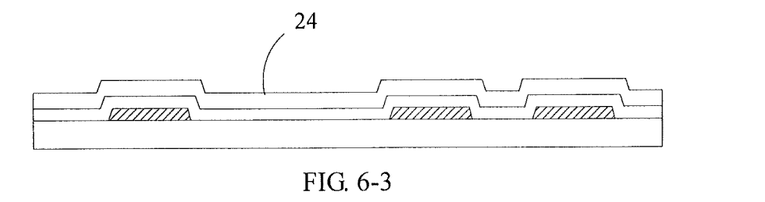
Figure 64:
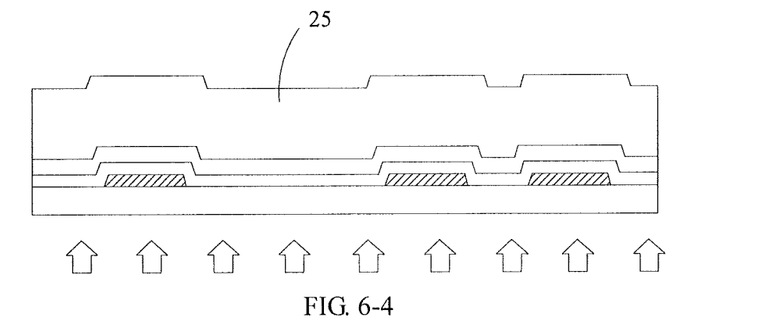

In step S202, an insulation layer 23, a transparent electrode layer 24, and a photoresist 25 are successively disposed on the gate 221, the gate lead 222, and the storage capacitor electrode 223, as shown in FIGS. 6-2, 6-3, and 6-4.

In this step, the insulation layer 23 is first deposited, as shown in FIG. 6-2. The insulation layer 23 may be a transparent film structure of a SiO2 film, a SiNX film, a multilayer film distributed by SiO2 and SiNX in a stack manner, or the like. After the insulation layer 23 is deposited, the transparent electrode layer 24 is deposited on the insulation layer 23, as shown in FIG. 6-3. Specifically, a transparent conducting material such as ITO, IZO, or GZO may be selected. Then, the photoresist 25 is coated on the transparent electrode layer 24 for subsequent photolithography use, as shown in FIG. 6-4.

Figure 65:
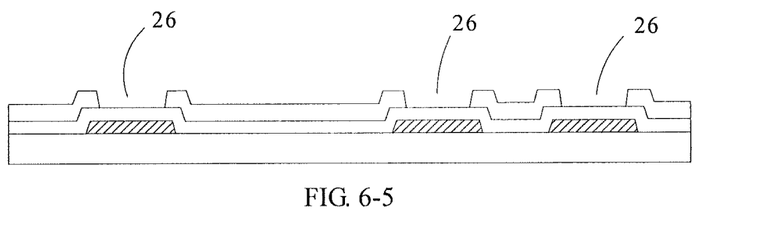

In step S203, the gate 221, the gate lead 222, and the storage capacitor electrode 223 are used as a mask to perform exposure from a back side of the substrate 21, and parts that are of the transparent electrode layer 24 and are aligned with the gate 221, the gate lead 222, and the storage capacitor electrode 223 are removed, so as to form a source 241 and a drain 242 that are aligned with the gate 221, as shown in FIGS. 6-4 and 6-5.

In this embodiment, the non-transparent gate 221, gate lead 222, and storage capacitor electrode 223 are used as a mask to perform exposure and development from the back side of the substrate 21, an exposed transparent electrode layer 24 is cured and kept, and a non-exposed part aligned with the gate 221, the gate lead 222, and the storage capacitor electrode 223 is peeled off together with the photoresist 25, so as to form channels 26 on an area above the gate 221, the gate lead 222, and the storage capacitor electrode 223, where the transparent electrode layer 24 at both sides of a channel 26 aligned with the gate 221 forms the source and the drain.

Figure 66:
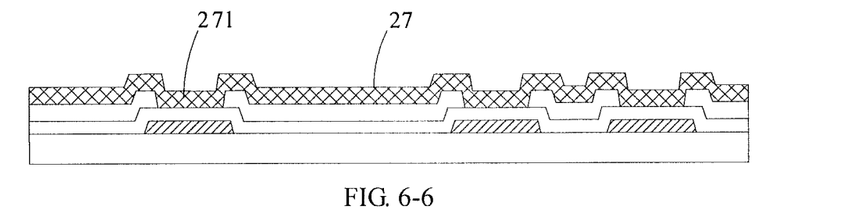

In step S204, a metal oxide semiconductor layer 27 is deposited on the source 241, the drain 242, and the other reserved part of the transparent electrode layer 24, as shown in FIG. 6-6.

Figure 67:
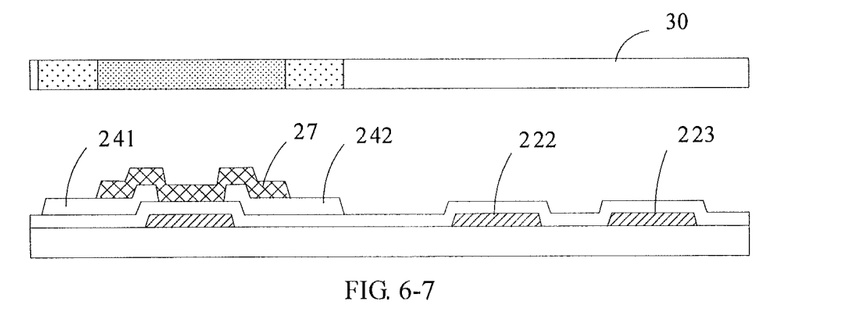

In step S205, the metal oxide semiconductor layer 27, the source 241, and the drain 242 are etched, so that outer ends of the source 241 and the drain 242 are exposed out of an etched metal oxide semiconductor layer 27, and in addition, a drain is isolated from a source of a different thin-film transistor component, as shown in FIG. 6-7.

As a preferred implementation manner of this embodiment, a second photolithographic mask, that is, a gray-tone mask 30 may be used to perform etching on the source 241, the drain 242, and the metal oxide semiconductor layer 27. An area of a corresponding transmittance of the gray-tone mask 30 is properly aligned with the to-be-etched source 241, drain 242, and metal oxide semiconductor layer 27, exposure is performed from a front side of the substrate 21, the transparent electrode layer 24 and the metal oxide semiconductor layer 27 on the gate lead 222 and the storage capacitor electrode 223 are etched, and the source 241, the drain 242, and the metal oxide semiconductor layer 27 on the gate 221 are etched in a ladder manner, so that outer ends of an etched source 241 and an etched drain 242 are exposed out of a reserved metal oxide semiconductor layer 27.

In this embodiment, a gray-tone mask is used to implement etching on the metal oxide semiconductor layer 27, the source, and the drain at the same time, and compared with a method for separately performing etching on a metal oxide semiconductor layer, a source, and a drain, a photolithography step is reduced and use of one photolithographic mask is reduced, which saves materials, simplifies a process, and also helps improve production efficiency.

Figure 68:
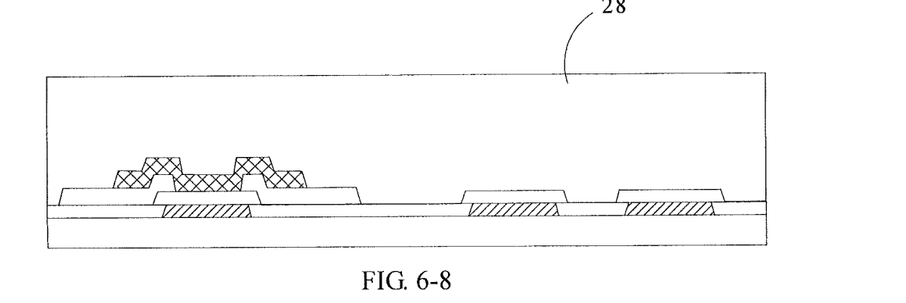
Figure 69:
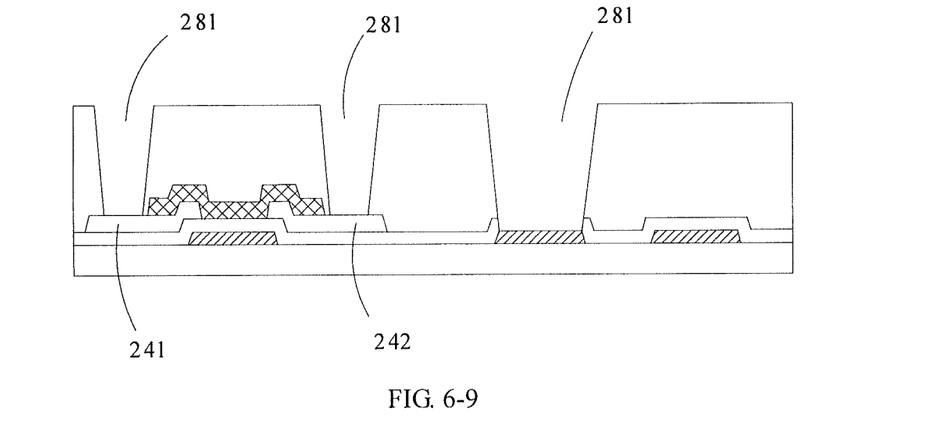
Figure 610:
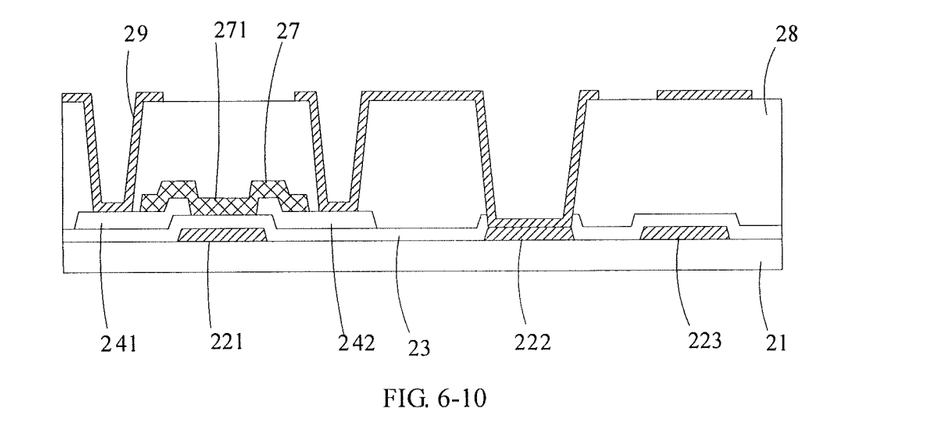

In step S206, a passivation layer 28 is deposited on the substrate 21, and the source 241, the drain 242, and the gate lead 222 are led out of the passivation layer 28, as shown in FIGS. 6-8, 6-9 and 6-10.

As one implementation manner of this embodiment, a third photolithographic mask may be used to perform etching on the passivation layer 28, so as to form a via 281 to the gate lead 222, a via 281 to a part of the source 241 that is exposed out of the metal oxide semiconductor layer 27, and a via 281 to a part of the drain 242 that is exposed out of the metal oxide semiconductor layer 27, and then a conducting material 29 is deposited to the passivation layer 28, where the conducting material is preferably a transparent conducting material, such as a transparent metal oxide, and the conducting material 29 covers the passivation layer 28 and is injected into the vias 281 to be in contact with the source 241, the drain 242, and the gate lead 222. Then, a fourth photolithographic mask is used to perform etching on the conducting material 29, so as to form a conducting lead to lead out the source 241, the drain 242, and the gate lead 222.

After the foregoing step is performed, the self-aligned metal oxide TFT pixel circuit is manufactured. It may be understood that the foregoing only describes a manufacturing process of a main structure of the pixel circuit, and certainly, the component further includes another regular function structure, and the circuit may be manufactured by using a regular method, which is not described again in the present invention.

In this embodiment of the present invention, a non-transparent bottom gate, gate lead, and storage capacitor electrode are used as a mask, and a source and a drain are automatically aligned with a gate through back exposure, so that a self-aligned metal oxide TFT pixel circuit with a bottom-gate bottom-contact structure is manufactured. This method has the same effect as the foregoing embodiment, and details are not described again in this embodiment.

An embodiment of the present invention further provides a metal oxide TFT pixel circuit, and the component may be manufactured by using the foregoing method.

Further, referring to FIG. 6-10, the component is a metal oxide TFT pixel circuit with a bottom-gate bottom-contact structure, and mainly includes a substrate 21. A gate 221, a gate lead 222, and a storage capacitor electrode 223 are disposed on the substrate 21 side by side, an insulation layer 23 is disposed on the gate 221 and the storage capacitor electrode 223, and a transparent source 241 and a transparent 242 are disposed side by side on an area that is on a surface of the insulation layer 23 and corresponding to the gate 221, in this case, a metal oxide semiconductor layer 27 is on the source 241 and the drain 242, the metal oxide semiconductor layer 27 forms a channel, that is, a semiconductor channel 271 that is between the source 241 and the drain 242 and may be used to transmit a carrier, and both sides of the semiconductor channel 271 are aligned with inner sides of the source 241 and the drain 242. In addition, a passivation layer 28 is disposed on the substrate 21, and all structures on the substrate 21 are sealed within the passivation layer. The source 241, the drain 242, and the gate lead 222 are led out of the passivation layer 28 by using a conducting material 29, so as to implement an electrical connection to an external circuit.

Further, the metal oxide semiconductor layer 27 may cover a part of the source 241 and a part of the drain 242, so that outer ends of the source 241 and the drain 242 are exposed out of the metal oxide semiconductor layer 27, and further preferably, the outer ends are exposed out of the metal oxide semiconductor layer 27 in a mutual symmetry manner. In addition, a via 281 to the gate lead 222, a via 281 to an exposed part of the source 241, and a via 281 to an exposed part of the drain 242 may be disposed on the passivation layer 28, where the vias 281 are filled with transparent conducting materials 29, and the source 241 and the drain 242 are led out of the passivation layer 28.

Further, the foregoing back exposure process is used, so that a width of an overlapped area of the source 241 and the semiconductor channel 271 that are of the component and a width of an overlapped area of the drain 242 and the semiconductor channel 271 that are of the component may be reduced to be less than 2 μm, which is far less than that of an overlapped area of a conventional component, thereby effectively reducing parasitic capacitance and improving component performance.

It may be understood that the self-aligned metal oxide thin-film transistor pixel circuit may further include another function structure, and details are not described again in this embodiment. In addition, any metal oxide thin-film transistor pixel circuit manufactured by using the foregoing method shall fall within the protection scope of the present invention.

The foregoing descriptions are merely exemplary embodiments of the present invention, but are not intended to limit the present invention. Any modification, equivalent replacement, and improvement made without departing from the spirit and principle of the present invention should fall within the protection scope of the present invention.

What is claimed is:

1. A manufacturing method of a self-aligned metal oxide thin-film transistor component, comprising:

preparing a non-transparent gate on a substrate;

successively disposing an insulation layer, a transparent electrode layer, and a photoresist on the gate;

using the gate as a mask to perform exposure from a back side of the substrate, an exposed part of the transparent electrode layer is cured and kept, and a non-exposed part of the transparent electrode layer aligned with the gate is peeled off together with the photoresist, thereby removing the non-exposed part that is of the transparent electrode layer and aligned with the gate, so as to form a source and a drain that are aligned with the gate;

depositing a metal oxide semiconductor layer on the source and the drain;

performing etching on the metal oxide semiconductor layer, the source, and the drain, so that outer ends of the source and the drain are exposed out of an etched metal oxide semiconductor layer, and isolating a drain from a source of a different thin-film transistor component; and depositing a passivation layer on the substrate, and leading the source and the drain out of the passivation layer.

2. The manufacturing method according to claim 1, wherein performing etching on the metal oxide semiconductor layer, the source, and the drain, so that outer ends of the source and the drain are exposed out of an etched metal oxide semiconductor layer, and isolating a drain from a source of a different thin-film transistor component includes:

using a gray-tone mask to perform photolithography once from a front side of the substrate, so that a patterned metal oxide semiconductor layer covers a part of the source and a part of the drain, and the outer ends of the source and the drain are exposed out of the metal oxide semiconductor layer, and isolating the drain from the source of the different thin-film transistor component.

3. The manufacturing method according to claim 2, wherein leading the source and the drain out of the passivation layer includes:

performing etching on the passivation layer, so as to form a via to a part of the source that is exposed out of the metal oxide semiconductor layer and a via to a part of the drain that is exposed out of the metal oxide semiconductor layer; and depositing conducting materials into the vias, so as to form a conducting lead to lead out the source and the drain.

4. The manufacturing method according to claim 3, wherein the conducting materials are transparent conducting materials.

5. A manufacturing method of a self-aligned metal oxide thin-film transistor pixel circuit, comprising:

preparing a gate, a gate lead, and a storage capacitor electrode which are not transparent on a substrate;

successively disposing an insulation layer, a transparent electrode layer, and a photoresist on the gate, the gate lead, and the storage capacitor electrode;

using the gate, the gate lead, and the storage capacitor electrode as a mask to perform exposure from a back side of the substrate, an exposed part of the transparent electrode layer is cured and kept, and non-exposed parts of the transparent electrode layer aligned with the gate, the gate lead, and the storage capacitor electrode are peeled off together with the photoresist, thereby removing the non-exposed parts that are of the transparent electrode layer and aligned with the gate, the gate lead, and the storage capacitor electrode, so as to form a source and a drain that are aligned with the gate;

depositing a metal oxide semiconductor layer on the source, the drain, and the other reserved part of the transparent electrode layer;

performing etching on the metal oxide semiconductor layer, the source, and the drain, so that outer ends of the source and the drain are exposed out of an etched metal oxide semiconductor layer, and isolating a drain from a source of a different thin-film transistor component; and depositing a passivation layer on the substrate, and leading the source, the drain, and the gate lead out of the passivation layer.

6. The manufacturing method according to claim 5, wherein performing etching on the metal oxide semiconductor layer, the source, and the drain, so that outer ends of the source and the drain are exposed out of an etched metal oxide semiconductor layer, and isolating a drain from a source of a different thin-film transistor component includes:

using a gray-tone mask plate to perform photolithography once from a front side of the substrate, and removing a part of the transparent electrode layer and a part of the metal oxide semiconductor layer that are of an area corresponding to the gate lead and the storage capacitor electrode, so that the outer ends of the source and the drain are exposed out of the etched metal oxide semiconductor layer, and isolating the drain from the source of the different thin-film transistor component.

7. The manufacturing method according to claim 6, wherein leading the source, the drain, and the gate lead out of the passivation layer includes:

performing etching on the passivation layer, so as to form a via to the gate lead, a via to a part of the source that is exposed out of the metal oxide semiconductor layer, and a part of the drain that is exposed out of the metal oxide semiconductor layer; and depositing conducting materials into the vias, so as to form a conducting lead to lead out the source, the drain, and the gate lead.

8. The manufacturing method according to claim 7, wherein the conducting materials are transparent conducting materials.

* * * * *